(12) United States Patent
Morris et al.

(10) Patent No.: US 7,223,243 B2
(45) Date of Patent: May 29, 2007

(54) THIN FILM ULTRASONIC TRANSMITTER/RECEIVER

(75) Inventors: Richard Franklin Morris, Stoughton, WI (US); Steven Taylor Morris, Madison, WI (US)

(73) Assignee: General Electric Co., Schenectady, NY (US)

( * ) Notice: Subject to any disclaimer, the term of this patent is extended or adjusted under 35 U.S.C. 154(b) by 331 days.

(21) Appl. No.: 10/932,530

(22) Filed: Sep. 2, 2004

(65) Prior Publication Data

US 2005/0103107 A1    May 19, 2005

Related U.S. Application Data

(63) Continuation-in-part of application No. 10/713,417, filed on Nov. 14, 2003.

(51) Int. Cl.
*A61B 8/00* (2006.01)

(52) U.S. Cl. .................. 600/459; 600/438; 310/334

(58) Field of Classification Search ........ 600/437–438, 600/443–447, 459; 73/618, 621, 625, 626; 310/314, 317–319, 334
See application file for complete search history.

(56) References Cited

U.S. PATENT DOCUMENTS

| | | | | | |
|---|---|---|---|---|---|
| 4,535,205 | A | * | 8/1985 | Ravinet et al. | 381/114 |
| 4,917,097 | A | * | 4/1990 | Proudian et al. | 600/463 |
| 5,109,861 | A | * | 5/1992 | Walinsky et al. | 600/463 |
| 5,166,573 | A | * | 11/1992 | Brown | 310/334 |
| 5,389,848 | A | * | 2/1995 | Trzaskos | 310/322 |
| 6,012,779 | A | | 1/2000 | Morris | |
| 6,305,060 | B1 | | 10/2001 | Morris | |
| 6,419,633 | B1 | * | 7/2002 | Robinson et al. | 600/443 |
| 6,775,388 | B1 | * | 8/2004 | Pompei | 381/191 |

* cited by examiner

*Primary Examiner*—Francis J. Jaworski

(57) ABSTRACT

A thin film piezoelectric material employs an array of metallic backer plates to provide high output, non-resonant ultrasonic transmission and reception suitable for ultrasonic measurement and/or imaging.

18 Claims, 1 Drawing Sheet

THIN FILM ULTRASONIC TRANSMITTER/RECEIVER

CROSS-REFERENCE TO RELATED APPLICATIONS

This application is a continuation-in-part of U.S. patent application Ser. No. 10/713,417 filed Nov. 14, 2003, hereby incorporated by reference.

BACKGROUND OF THE INVENTION

The present invention relates to ultrasonic acoustic combination receivers and transmitters, such as may be used in quantitative ultrasonic imaging and measurements, and in particular to an improved thin film receiver/transmitter.

Quantitative ultrasonic imaging is used, for example, in bone densitometry where ultrasound is transmitted through in vivo bone, most typically the os calcis of the heel, in order to measure trabecular bone. Common measurements made by such densitometers include the speed of sound (SOS) and broadband ultrasonic attenuation (BUA) in the bone. Images of the bone based on these or other measurements may also be provided by the densitometer. Densitometers of this type are described in U.S. Pat. Nos. 5,840,029 and 6,517,487, assigned to the assignee of the present invention, and hereby incorporated by reference.

Ceramic transducers are commonly used as the transmitting ultrasonic transducer in such densitometers because of their high output signals. In this application, the mechanical resonance of the ceramic transducer is adjusted to be near the principal frequency being transmitted. Operation in this "resonant" mode increases the output of the transducer, but can make manufacturing of the transducer difficult because of the high sensitivity of the transducers resonant frequency to variations in the dimensions of the many subcomponents of the transducer. Slight differences in resonant frequencies of the transducers on different machines complicate the effort to provide highly repeatable measurements that are machine independent. Significant differences in transmission frequencies can affect quantitative measurements such as assessments of bone density.

Thin film polymer piezoelectric materials such as polyvinylidene fluoride (PVDF) may also be used as a receiving ultrasonic transducer as described in U.S. Pat. No. 6,305,060 issued Oct. 23, 2001, and U.S. Pat. No. 6,012,779 issued Jan. 11, 2000 assigned to the assignee of the present invention and hereby incorporated by reference. Application of PVDF to transmitting ultrasonic transducers has been limited because of low output levels.

SUMMARY OF THE INVENTION

The present invention provides an ultrasonic transmitter and receiver using a piezoelectric film and suitable for use in ultrasonic imaging systems. The transducer provides suitable output levels and may operate in a non-resonant mode avoiding some of the difficulties of manufacturing present ceramic transducers. The non-resonant mode also allows rapid sequential transmission and reception of ultrasonic signals from local targets (for example, in medical imaging) without interference from transducer ringing.

Generally, the invention employs a set of thin metallic backer electrodes attached to the piezoelectric film that provides a sharp discontinuity in acoustic impedance at the back surface of the piezoelectric film to increase the acoustic output from the piezoelectric film's front surface during transmission. During reception, each of the backer electrodes operates independently to provide spatial discrimination necessary for most quantitative applications. During transmission, the backer electrodes operate in unison, for example, as a ground plane. The metallic backer electrodes may be copper adhered to a printed circuit board further simplifying the manufacturing process.

DETAILED DESCRIPTION OF THE PREFERRED EMBODIMENT

Figure 1:
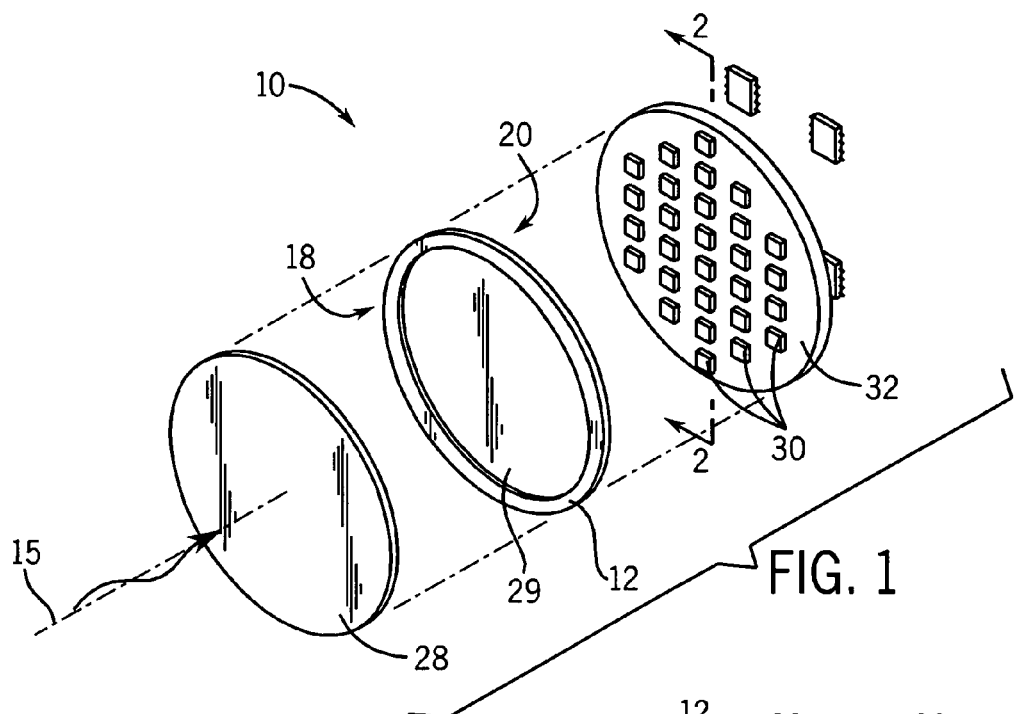
FIG. 1 is a perspective, exploded view of the ultrasonic transducer of the present invention showing a protective acoustically transparent layer followed by a thin film piezoelectric material, a metallic backer electrode and support structure.

Referring now to FIG. 1, an ultrasonic transmitting and receiving transducer 10 constructed according to the present invention includes a disk-shaped piezoelectric film 12. In the preferred embodiment, the piezoelectric film 12 may be a polyvinylidene fluoride film (PVDF) that has been polarized to create piezoelectric properties according to methods well understood in the art.

A front face 18 of the piezoelectric film 12 is preferably coated with a thin flexible layer of conductive material such as copper. This front electrode 29 may be coated with nickel to reduce corrosion. These materials may be applied by vacuum metallization or electroplating or other methods and creates a front electrode 29 which is continuous. The electrode may also be sub-divided into multiple elements such as to allow individual stimulus to various parts of the assembly. Devices organized in this manner would be capable of generating a focused or otherwise directed sound beam.

The front face 18 of the piezoelectric film 12 and the front electrode 29 may be covered by an acoustically transparent protective film 28 such as Teflon to prevent direct contact between water or other acoustic coupling medium (providing a path between the ultrasonic transmitting and receiving transducer 10 and an imaged object such as a bone or organ of a patient).

Figure 2:
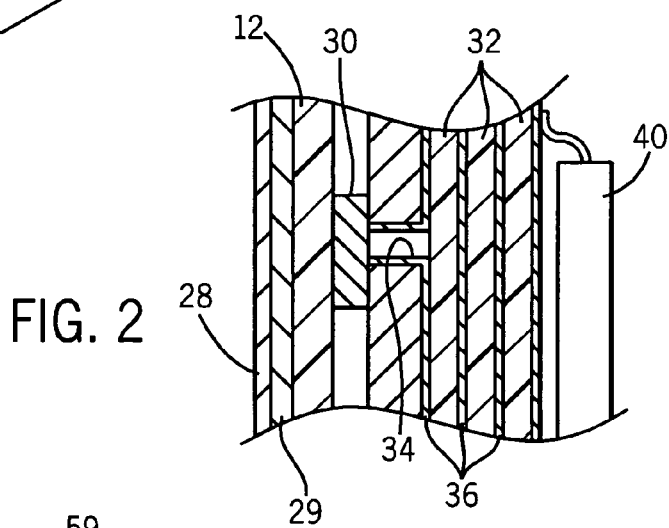
FIG. 2 is a fragmentary, elevational cross section through the transducer of FIG. 1 showing the layers of the transducer as assembled and the connection of electrodes to opposite sides of the piezoelectric material.

Referring also to FIG. 2, a rear face 20 of the piezoelectric film 12 abuts a series of backer electrodes 30 supported in the preferred embodiment on a printed circuit board 32. Each of the backer electrodes 30 in the preferred embodiment are squares, disks, or other shapes as an application may require of copper approximately 0.025 inches thick arranged in vertical columns and horizontal rows or other pattern and spaced apart to allow mutual electrical isolation over the area of the piezoelectric film 12. This thickness is thicker than the 20 mil copper cladding normally obtainable on standard printed circuit board material and is preferably much less than ¼ wavelength of the relevant ultrasonic transmission frequency and less than 0.050 inches thick. The spacing of the squares of copper partially define the fundamental resolution of the ultrasonic transmitting and receiving transducer 10 when receiving, and may be varied accordingly.

In the preferred embodiment, the backer electrodes 30 abut the rear face 20 of the piezoelectric film 12 with or without intervening conductive material. In this case, the backer electrodes 30 capacitively couple to the rear face 20 of the piezoelectric film 12. However, it will be recognized that in an alternative embodiment, a conductive paste or epoxy or the like may be used.

The metal of the backer electrodes 30 has an acoustic impedance substantially different from the material of the piezoelectric film 12 to reduce, but not eliminate, acoustic coupling between the two.

Referring now to FIG. 2, the backer electrodes 30 may be attached to a front face of a printed circuit board 32 at the sites of conductive plate-through holes 34 in the printed circuit board 32. This attachment may be by conventional soldering techniques. The use of separate backer electrodes soldered to the printed circuit board 32 overcomes limitations on standard copper cladding thickness in commercial clad printed circuit boards. The metal of the metallic backer electrodes 30 has an acoustic impedance different from that of the substrate of the printed circuit board 32 (e.g. fiberglass epoxy) minimizing acoustic transmission through this interface as will be understood to those of ordinary skill in the art.

The plate-through holes 34 may connect via conductive traces 36 in multiple layers of the printed circuit board 32 to integrated circuits 40 attached to the rear surface of the printed circuit board 32. The integrated circuits 40 provide input signal processing such as multiplexing, and amplification as will be described.

Figure 3:
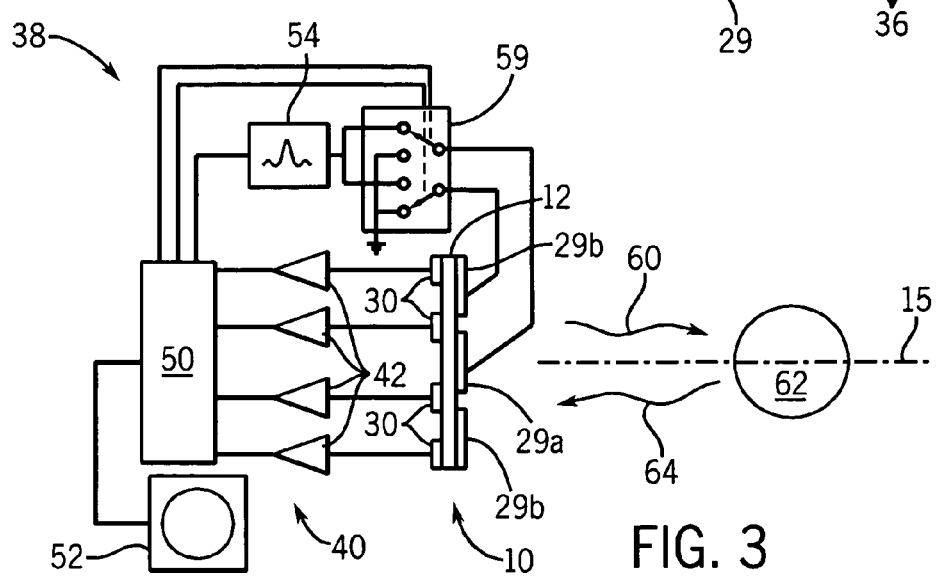
FIG. 3 is a block diagram of a quantitative ultrasonic apparatus using the transducer of the present invention.

Referring now to FIG. 3 in the preferred embodiment for use in a ultrasonic imaging machine 38, the controller 50, operating in a transmission mode, activates a signal generator 54 to provide a high voltage electrical signal applied through a switch 59 to the electrode 29 to stimulate the piezoelectric film 12. The signal generator 54 may, for example, provide a 500 KHz wide band pulse referenced to a fixed crystal oscillator. The switch 59 is a solid-state switch controlled by the controller 50 to alternately connect the electrode 29 to either the signal generator 54 or to ground or a functionally similar source of constant voltage. Alternatively, multiple generators could be used to generate focused or otherwise controlled transmit waves. Contact with electrode(s) 29 may be made through thin wires or flexible circuit elements passing from the circuit card to the front face of the piezoelectric film 12.

The voltage of the signal generator 54, when applied with respect to the virtual ground of the backer electrodes 30, produces a transmitted ultrasonic signal 60.

When so energized, the piezoelectric film 12 will direct the transmitted ultrasonic signal 60 generally along a longitudinal axis 15 perpendicular to the front face 18 of the piezoelectric film 12. Most of the signal directed along longitudinal axis 15 toward the rear face 20 is reflected at the boundary between the piezoelectric film 12 and the backer electrodes 30 which have distinctly different acoustic impedances. While the inventor does not wish to be bound by a particular theory, it is believed that the small signal passing into the backer electrodes 30 is reflected at the interface between the backer electrodes 30 and the printed circuit board 32.

Immediately after transmission of the transmitted ultrasonic signal 60, the controller 50 changes the switch 59 to connect the electrode 29 to ground or other constant voltage reference.

Each backer electrode 30 is connected to a separate transconductance amplifier 42 operating so that the input of the amplifier 42 connected to the backer electrode 30 is at a virtual ground. The output from each of the amplifiers 42 may then be received by a controller 50 providing for the necessary sampling and digitization of the amplifier output signals. The controller 50 may then execute a stored program to process these signals according to methods well known in the art to produce a B-mode ultrasonic image and/or a quantitative measurement of an imaged object then presented on a display console 52.

In typical B-mode operation, the transmitted ultrasonic signal 60 from the ultrasonic transmitting and receiving transducer 10 will proceed to a target 62 in front of the ultrasonic transmitting and receiving transducer 10 to produce an echo ultrasonic signal 64 returning to the ultrasonic transmitting and receiving transducer 10. When the echo ultrasonic signal 64 strikes the piezoelectric film 12, piezoelectric voltages may be detected at the backer electrodes 30 to be received by the amplifiers 42 and forwarded to the controller 50.

When the target is relatively close to the transducer 10, it is important that vibrations of the piezoelectric film 12 from the transmission of transmitted ultrasonic signal 60 have died out prior to receipt of echo ultrasonic signal 64. This is practical because of the non-resonant operation of the piezoelectric film 12 relative to conventional ceramic transducers.

The ultrasonic transmitting and receiving transducer 10 is essentially non-resonant at ultrasonic frequencies as defined both by center frequency and Q and has a lower construction cost than a ceramic device. The ultrasonic transmitting and receiving transducer 10 can have an operating bandwidth of 3 MHz or more compared to a 300 KHz bandwidth achievable with ceramic transducers.

Because of the low resonance of the ultrasonic transmitting and receiving transducer 10, the output wave is not colored by resonant characteristics providing improved device-to-device consistency. Although the present inventors do not wish to be bound by a particular theory, they believe that the thin film piezoelectric film 12 has an additional advantage over ceramic as a transmitter in that it provides very little lateral mode wave such as improves beam profile produced by the ultrasonic transmitting and receiving transducer 10.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasonic transmitter/receiver comprising:
    a piezoelectric polymer film adapted to transmit an ultrasonic acoustic signal from a front face along a signal path and to receive an ultrasonic acoustic signal at the front face along the signal path;
    a front electrode applied to the front face of the piezoelectric polymer film;
    a plurality of electrically independent and substantially rigid metallic backer electrodes adhered to a rear face of the piezoelectric polymer film;
    a plurality of amplifiers connected to each of the plurality of metallic backer electrodes to detect electrical signals there from; and
    a transmit circuit connected between the front electrode and at least one of the metallic backer electrodes to apply an electrical voltage therebetween to transmit an ultrasonic acoustic signal, wherein the amplifiers present a virtual ground point at their inputs and the transmit circuit applies a voltage to the front electrode with respect to this virtual ground.

2. The ultrasonic transmitter/receiver of claim 1 wherein the metallic backer electrodes have a thickness along the signal path of substantially less than one-quarter wavelength of the acoustic signal.

3. The ultrasonic transmitter/receiver of claim 1 wherein the metallic backer electrodes directly abut the piezoelectric polymer film.

4. The ultrasonic transmitter/receiver of claim 1 wherein the backer electrodes are copper and are supported on a printed circuit board and have a thickness of no less than 20 mils.

5. The ultrasonic transmitter/receiver of claim 1 wherein the metallic backer electrodes are arranged in a regular pattern.

6. The ultrasonic transmitter/receiver of claim 1 further including a support structure supporting the metallic backer electrodes and having an acoustic impedance substantially different from the metallic backer electrodes.

7. The ultrasonic transmitter/receiver of claim 6 wherein the support structure is a polymer material.

8. The ultrasonic transmitter/receiver of claim 1 wherein the piezoelectric polymer film is disk-shaped.

9. The ultrasonic transmitter/receiver of claim 1 wherein the electrical voltage produced by the transmit circuit provides energy concentrated at frequencies substantially removed from a natural resonance of the piezoelectric polymer film.

10. The ultrasonic transmitter/receiver of claim 1 wherein the metallic backer electrodes are substantially less than ¼ wavelength of a frequency of the acoustic signal in thickness.

11. The ultrasonic transmitter/receiver of claim 1 wherein the metallic backer electrodes are less than 0.05 inches thick.

12. The ultrasonic transmitter/receiver of claim 1 wherein the metallic backer electrodes are substantially 0.025-inch thick copper.

13. The ultrasonic transmitter/receiver of claim 1 wherein the piezoelectric polymer film is PVDF.

14. An imaging ultrasound device comprising:
a piezoelectric polymer film adapted to transmit an ultrasonic acoustic signal from a front face along a signal path and to receive an ultrasonic acoustic signal at the front face along the signal path;
a front electrode applied to the front face of the piezoelectric polymer film;
a plurality of electrically independent and substantially rigid metallic backer electrodes adhered to a rear face of the piezoelectric polymer film;
a pulse circuit connected between the front electrode and at least one of the metallic backer electrodes to apply an electrical voltage therebetween to transmit an ultrasonic acoustic signal;
a plurality of amplifiers connected to each of the plurality of metallic backer electrodes to detect an ultrasonic signal received along the signal path; and
processing circuitry for receiving output from the plurality of amplifiers to construct an ultrasonic image based on received echoes of a signal transmitted by the piezoelectric polymer film received by the piezoelectric polymer film, wherein the amplifiers present a virtual ground point at their inputs and the pulse circuit applies a voltage to the front electrode with respect to this virtual ground.

15. The imaging ultrasound device of claim 14 wherein the metallic backer electrodes have a thickness of substantially less than one-quarter wavelength of the acoustic signal along the signal path.

16. The imaging ultrasound device of claim 14 wherein the metallic backer electrodes directly abut the piezoelectric polymer film.

17. The imaging ultrasound device of claim 14 wherein the backer electrodes are copper cladding on a printed circuit board having a thickness of no less than 20 mils.

18. The imaging ultrasound device of claim 14 wherein the metallic backer electrodes are arranged in a regular pattern.

* * * * *